United States Patent
Jaffray et al.

(10) Patent No.: US 8,160,675 B2
(45) Date of Patent: Apr. 17, 2012

(54) RETROSPECTIVE SORTING OF 4D CT INTO BREATHING PHASES BASED ON GEOMETRIC ANALYSIS OF IMAGING FIDUCIALS

(75) Inventors: David A. Jaffray, Etobicoke (CA); Michael R. Kaus, Toronto (CA); Jeremy D. P. Hoisak, Toronto (CA); Thomas G. Purdie, Oakville (CA)

(73) Assignee: Koninklijke Philips Electronics N.V., Eindhoven (NL)

( * ) Notice: Subject to any disclaimer, the term of this patent is extended or adjusted under 35 U.S.C. 154(b) by 646 days.

(21) Appl. No.: 12/300,340

(22) PCT Filed: May 1, 2007

(86) PCT No.: PCT/US2007/067847
§ 371 (c)(1), (2), (4) Date: Nov. 11, 2008

(87) PCT Pub. No.: WO2007/136967
PCT Pub. Date: Nov. 29, 2007

(65) Prior Publication Data
US 2009/0116719 A1    May 7, 2009

Related U.S. Application Data

(60) Provisional application No. 60/747,451, filed on May 17, 2006.

(51) Int. Cl.
*A61B 5/05* (2006.01)
(52) U.S. Cl. ........ 600/425; 600/424; 600/426; 382/128; 382/130; 382/131

(58) Field of Classification Search .................. 382/128, 382/130, 131; 600/425, 428, 435; 378/7
See application file for complete search history.

(56) References Cited

U.S. PATENT DOCUMENTS

| | | | |
|---|---|---|---|
| 3,547,121 | A | 12/1970 | Cherry |
| 4,838,265 | A | 6/1989 | Cosman et al. |
| 4,860,331 | A | 8/1989 | Williams et al. |
| 5,469,847 | A | 11/1995 | Zinreich et al. |
| 2006/0074292 | A1 | 4/2006 | Thomson et al. |
| 2006/0074300 | A1 | 4/2006 | Green |

(Continued)

FOREIGN PATENT DOCUMENTS

JP    06269445 A    9/1994

OTHER PUBLICATIONS

Berlinger, K., et al.; A simple method for labeling CT images with respiratory states; 2006; Med. Phys.; 33(9) 3144-3148.

(Continued)

*Primary Examiner* — Tse Chen
*Assistant Examiner* — Baisakhi Roy (57) ABSTRACT

A respiratory marker (40, 140, 240, 340, 440) includes an elongated detectable portion (42, 342, 442) that is operatively coupled with respiration of an imaging subject such that the elongated detectable portion moves with the respiration. The elongated detectable portion is arranged to intersect images acquired by an imaging scanner (10) at different times and at different positions along a scanner axis (20), and is detectable as a marker feature in the images. A marker position finder (52, 54) is configured to determine positions of the marker features in the images.

14 Claims, 5 Drawing Sheets

U.S. PATENT DOCUMENTS

2006/0093089 A1* 5/2006 Vertatschitsch et al. ........ 378/65
2010/0036241 A1* 2/2010 Mayse et al. .................. 600/435

OTHER PUBLICATIONS

Klahr et al., Respiratory-correlated multislice CT for radiation therapy planning: imaging and visualization methods, Medicamundi 49/3, pp. 34-37, (2005).

Fitzgibbon et al., Direct Least Square Fitting of Ellipses, IEEE Transactions on Pattern Analysis and Machine Intelligence, vol. 21, No. 5, pp. 476-480, (1999).

Grass et al., Helical cardiac cone beam reconstruction using retrospective ECG gating, Institute of Physics Publishing, Phys. Med. Biol. 48, pp. 3069-3084, (2003).

Pan et al., 4D-CT imaging of a volume influenced by respiratory motion on multi-slice CT, Am. Assoc. Phys. Med., Medical Physics, vol. 31, No. 2, pp. 333-340, (2004).

Vedam, S. S., et al.; Determining parameters for respiration-gated radiotherapy; 2001; Med. Phys.; 28(10)2139-2146.

* cited by examiner

RETROSPECTIVE SORTING OF 4D CT INTO BREATHING PHASES BASED ON GEOMETRIC ANALYSIS OF IMAGING FIDUCIALS

CROSS REFERENCE TO RELATED APPLICATIONS

This application claims the benefit of U.S. provisional application Ser. No. 60/747,451 filed May 17, 2006, which is incorporated herein by reference.

The present application relates to the three-dimensional imaging arts. It finds particular application in three-dimensional computed tomography imaging, and is described with particular reference thereto. However, the following will find application in other imaging modalities, such as positron emission tomography (PET), single-photon emission computed tomography (SPECT), and so forth.

Computed tomography imaging is used for numerous applications which call for precise positional registry. For example, computed tomography imaging is sometimes used to image malignant tumors and surrounding tissue and organs, with the images used in planning radiotherapy treatment sessions. The computed tomography image features should be registered with the geometry of the radiotherapy apparatus to make such planning effective. In interventional imaging, computed tomography imaging is used to guide insertion of a catheter, biopsy needle, or other interventional instrument. As yet another example, in multi-modal imaging the computed tomography images are spatially registered with images acquired by one or more other modalities, such as magnetic resonance imaging, positron emission tomography, or so forth.

When imaging features in the thoracic region or elsewhere, the spatial registration or alignment of computed tomography images preferably takes into account respiratory motion. It is known to do so by measuring abdominal movement concurrently with the tomographic imaging. In some approaches, optical markers are disposed on the patient, and the motion of these optical markers is monitored by a video camera or other optical sensor. The respiratory cycle is then derived from the observed motion of the optical markers. Reconstructed slice images are then sorted, binned, or otherwise organized based on respiratory phase to enable accounting for respiratory motion.

Such approaches have certain difficulties, however. For example, it is necessary to synchronize, separately record and store the respiratory and imaging data. The separate respiratory monitoring and imaging datasets must then be correlated based on time stamps or the like. Any error in the time correlation between these two datasets, such as a time offset error between the respiratory monitoring and imaging datasets, can produce substantial systematic error in the respiratory phase binning of the image slices. Additionally, the respiratory monitoring requires a dedicated CCD camera, strain gauge, magnetic beacon, or other dedicated respiratory sensor positioned closely adjacent the imaging region. Optical and mechanical (e.g., strain gauge) sensors inhibit patient access and add bulk to the imaging system, while magnetic-based sensors are incompatible with imagers such as magnetic resonance scanners. Further, the cameras or other dedicated sensors should be recalibrated periodically to correct miscalibration and systematic error. Still further, for proper operation a direct line-of-sight between the optical markers and the camera must be maintained throughout the imaging acquisition period. To accommodate a variety of patient sizes and shapes while maintaining unobstructed lines-of-sight, redundant cameras and extra bulk may be needed. Further, the use of other equipment is encumbered by the need to maintain unobstructed lines-of-sight.

In accordance with one aspect, respiratory marker is disclosed. A detectable portion is arranged to intersect images acquired at different positions along a scanner axis of an imaging scanner and is detectable as a marker feature in images acquired by the imaging scanner at different times and at different positions along the scanner axis.

In accordance with another aspect, an apparatus is disclosed for organizing images acquired by an imaging scanner at different times and at different positions along a scanner axis. A respiratory marker includes an elongated detectable portion that is operatively coupled with respiration of an imaging subject such that the elongated detectable portion moves with the respiration. The elongated detectable portion is arranged to intersect the images acquired at different times and at different positions along the scanner axis and is detectable as a marker feature in the images. A marker position finder is configured to determine positions of the marker features in the images.

In accordance with another aspect, a method is disclosed for organizing images acquired at different times with a respiratory marker arranged to be detectable as a marker feature in the acquired images. A position of the marker feature in a selected acquired image is determined. A respiration phase is assigned for the selected acquired image based on the determined position of the marker feature. The determining and assigning operations are repeated to assign respiration phases to the images acquired at different times.

In accordance with another aspect, a digital medium is disclosed storing processor-executable instructions for performing the method as set forth in the preceding paragraph.

One advantage is that respiratory monitoring data is embedded directly with the imaging data, avoiding the need to store and temporally synchronize separate respiratory monitoring and imaging data sets.

Another advantage is that, by embedding the respiratory monitoring data with the imaging data, synchronization is automatically achieved and time offset errors between the respiratory monitoring data and the imaging data are avoided.

Another advantage is that respiratory monitoring data is acquired directly by the imaging system without the use of additional sensing equipment.

Another advantage is that no optical sensor line-of-sight or other geometrical constraint is imposed on positioning of the patient in the imaging system.

Still further advantages of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

Figure 1:
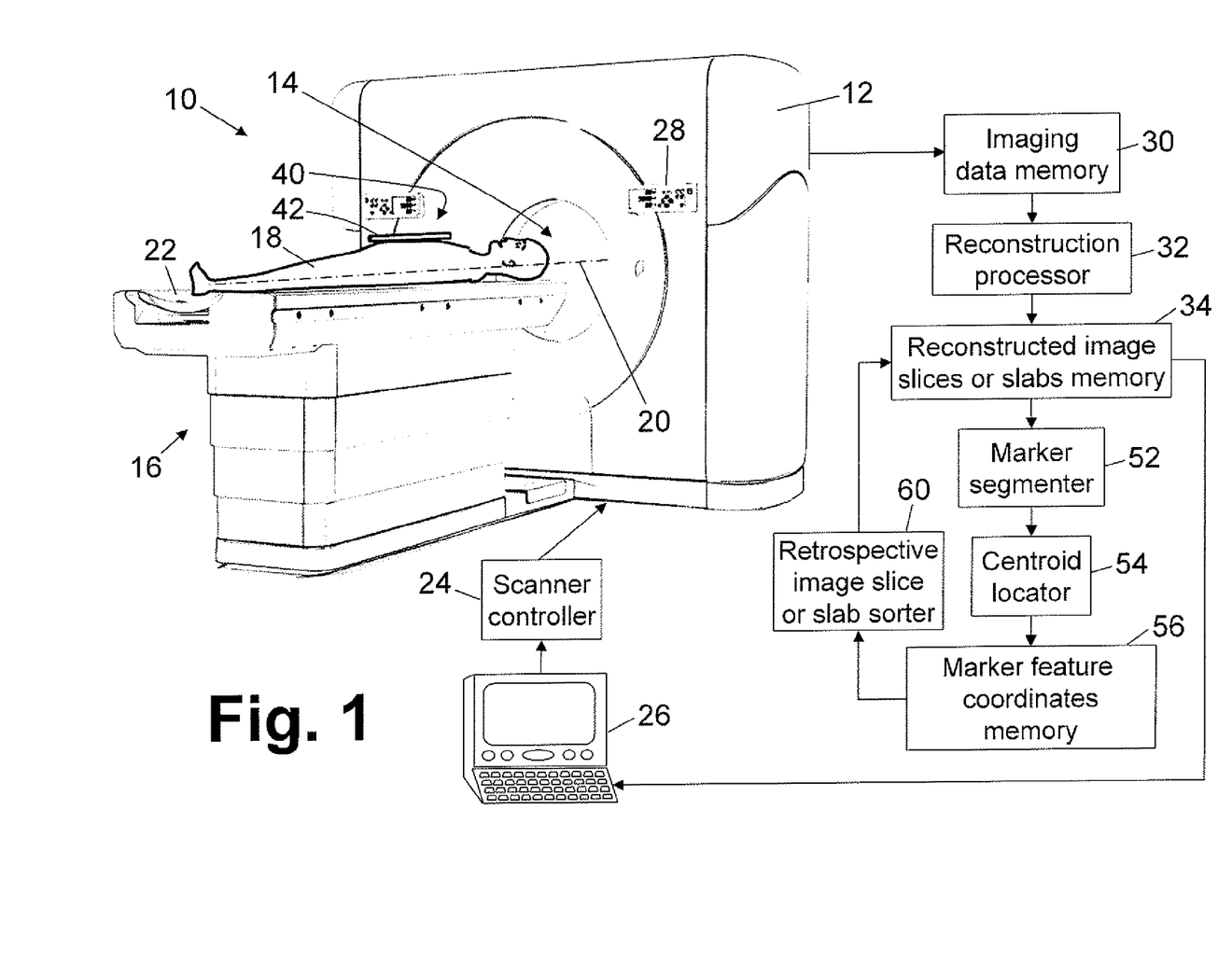
FIG. 1 diagrammatically shows a computed tomography imaging system including respiratory monitoring.

With reference to FIG. 1, a computed tomography (CT) scanner 10 includes a stationary housing 12 defining an imaging region 14, and a subject support 16 that supports a medical patient, animal, or other imaging subject 18 that respires in accordance with a respiration cycle or undergoes other cyclic motion. The housing 12 includes components suitable for performing transmission x-ray tomography projection data acquisition for imaging a slice, slab, or other region. Some suitable components may include, for example, an x-ray tube and an x-ray detector array mounted on opposite sides of the imaging region 14 on an rotating gantry disposed in the housing 12 (x-ray tube, detector array, and rotating gantry not shown but contained in the housing 12). The illustrated scanner 10 is a diagrammatic representation of a Brilliance™ CT scanner (available from Koninklijke Philips Electronics N.V., Eindhoven, the Netherlands); however, substantially any type of CT scanner can be used, as well as other types of imaging scanners such as positron emission tomography (PET) scanners, single-photon emission computed tomography (SPECT) scanners, magnetic resonance imaging (MRI) scanners, and so forth. The scanner 10 scans the imaging subject 18 by relatively moving the subject and the imaging region 14 along a scanner axis 20. In the illustrated scanner 10, this is accomplished by keeping the housing 12 and imaging region 14 stationary and translating a support table 22 on which the subject 18 rests along the scanner axis 20 through the imaging region 14. However, it is also contemplated to keep the imaging subject stationary and to translate an operative portion of the scanner; for example, the Skylight™ nuclear camera (not shown; available from Koninklijke Philips Electronics N.V., Eindhoven, the Netherlands) employs detector heads on robotic arms that can translate along the scanner axis relative to a stationary patient to scan the patient along the scanner axis.

The scanning can be done in various ways. In a multi-slice approach, the imaging subject 18 remains stationary respective to the imaging region 14 during acquisition of projection data corresponding to a slice, stab formed of a set of adjacent slices, or other imaging region. After acquisition of data for the two-dimensional or thin three-dimensional slice is complete, the imaging subject 18 is then advanced a selected distance or step along the scanner axis 20 so that another slice that is adjacent to, partially overlapping, or spaced apart from, the previous slice or slab is positioned in the imaging region 14. Imaging data for this new slice are acquired, and the subject 18 is again advanced a selected distance or step, and so forth, so as to acquire imaging data for a plurality of slices along the scanner axis 20.

In a continuous approach, the subject 18 is continuously advanced along the scanner axis 20 as projection data is acquired. For the illustrated computed tomography scanner 10, this typically results in a helical orbit of the x-ray source and x-ray detector array about the imaging subject 18; hence, this approach is sometimes called "helical CT". For some other imaging modalities, such as PET, the detectors do not rotate. The acquired imaging data is suitably binned into sets of data each acquired over a short time interval that are suitable for reconstruction into an image of a slice, slab, or other region.

As another example, in the case of magnetic resonance imaging, both the scanner imaging components and the imaging subject are typically stationary, and images are acquired at different positions along a scanner axis by applying suitable slice-, slab-, or other region-selective magnetic field gradients. In some magnetic resonance scanners, the patient is disposed in a cylindrical bore defined by the housing, and magnetic resonance images are acquired as two-dimensional or thin three-dimensional slices transverse to and spaced-apart along a scanner axis that is coincident with the axis of the cylindrical bore. In some cases, the spaced-apart slices or slabs may be partially overlapping. In closed-bore systems, the bore is typically closed except for openings at one or (more typically) both ends. In open-bore systems, the cylindrical bore additionally includes a longitudinal opening that provides a less claustrophobic patient setting and facilitates more convenient access to the patient by medical personnel.

With returning reference to the computed tomography example of FIG. 1, regardless of whether scanning is done in a step-wise (e.g., multi-slice) or continuous (e.g., helical) manner, the imaging scanner 10 is suitably controlled by a scanner controller 24 that receives scan parameters, recipes, or other user selection inputs via a user interface 26. In the illustrated embodiment, the user interface 26 is also used to display images generated by the imaging scanner 10, and in some embodiments the user interface 26 is further used for diagnostic image analyses. In other embodiments, a separate graphical user interface is provided for image viewing and optional analysis. In some embodiments, the imaging scanner 10 includes scanner-mounted controls 28 that substitute for controls of the user interface 26, or that duplicate controls of the user interface 26, or that provide additional or alternative controls for operating the imaging scanner 10.

With continuing reference to FIG. 1, the acquired imaging data, such as projection data in the illustrated example of computed tomography, are stored in an imaging data memory 30. A reconstruction processor 32 reconstructs images from imaging data acquired by the imaging scanner 10 at different times and at different positions along the scanner axis 20 to produce a set of images acquired by the imaging scanner 10 at different times and at different positions along a scanner axis 20. The reconstructed image acquired at different times and at different positions along a scanner axis 20 are suitably stored in a memory 34. It is to be appreciated that the memories 30, 34 may be electrical memory (e.g., RAM memory, FLASH memory, or so forth), magnetic memory (e.g., a hard disk), optical memory (e.g., an optical disk), or another volatile or non-volatile memory.

In the illustrated case of a computed tomography scanner 10, the reconstructed images acquired by the imaging scanner 10 at different times and at different positions along a scanner axis 20 are typically two-dimensional slice images, or thin three-dimensional slice images having some finite thickness or number of voxels along the dimension of the scanner axis 20. For example, the illustrated Brilliance™ CT scanner is available with detector arrays suitable for simultaneously imaging six slices (e.g., each image slab consists of six slices, or equivalently has a thickness of six voxels, in the multi-slice imaging mode), ten slices, sixteen slices, or so forth. Each image is acquired over a relatively short period of time relative to the period of the respiratory cycle of the imaging subject 18, and is hence acquired at about a single respiratory phase. In a high-speed computed tomography scanner, the rotating gantry may rotate at 300 rpm or faster, enabling acquisition of imaging data for many slices per minute. On the other hand, the imaging data from which are reconstructed the slice images acquired at different positions along the scanner axis 20 are acquired at substantially different times, and hence generally have different corresponding respiratory phases. For example, the plurality of slice or slab images may comprise a CINE or 4D-CT dataset spanning a substantial portion of a respiratory cycle, or spanning a whole respiratory cycle, or spanning a plurality of respiratory cycles.

With continuing reference to FIG. 1, in order to assign a respiration phase (or respiratory phase) to each acquired image, a respiratory marker 40 including an elongated detectable portion 42 is arranged to intersect the images of slices or other regions acquired at different times and at different positions along the scanner axis. At least the detectable portion 42 of the respiratory marker 40 is detectable (for example, visible, or leaving a characteristic spatially localized image representation or artifact, or so forth) as a marker feature in the images. For the illustrated example of computed tomography, detectability of the elongated detectable portion 42 is suitably achieved by including in the elongated detectable portion 42 a material that is at least partially opaque or absorbent to the x-rays or other radiation used in the computed tomography imaging. For example, if the elongated detectable portion 42 is made of wood, plastic, or high-density foam, then it will be visible in slice or slab images acquired by computed tomography scanners employing an x-ray radiation source. On the other hand, a more dense material such as metal is generally less suitable, since a metal marker will tend to produce shadowing, streaking, or other artifacts in the reconstructed images slices or slabs. For computed tomography a material having x-ray absorbance about the same as that of water or human tissue is advantageous. In magnetic resonance imaging scanners, a material which is resonant at a frequency at or near the magnetic resonance frequency is advantageous. For SPECT and PET, the elongated detectable portion may include a radioactive substance to provide detectability respective to the radiation detectors. For example, the elongated detectable portion for SPECT or PET may include a hollow tube containing a liquid that includes the radioactive substance. The radioactive substance may be the same as or different from the radiopharmaceutical used for the SPECT or PET imaging. It is to be appreciated that because the elongated detectable portion 42 is elongated and extends through the images at different positions along the scanner axis 20, a corresponding marker feature will be detectable in each acquired image. The respiratory marker 40 is further operatively coupled with respiration of the imaging subject 18 such that the elongated detectable portion 42 moves with the respiration.

Figure 2:
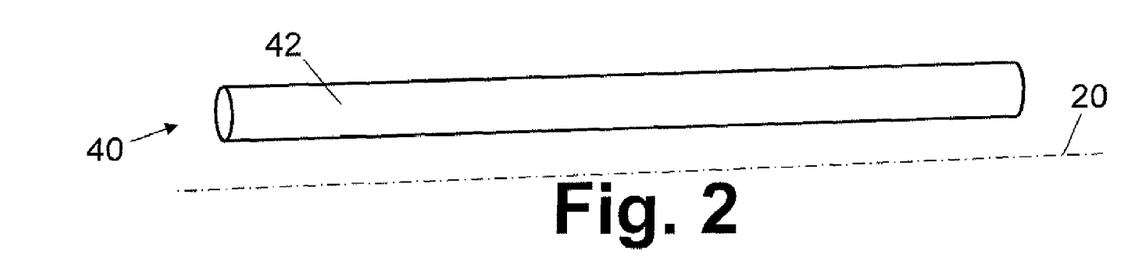
FIG. 2 shows a perspective view of the respiratory marker used in the system of FIG. 1.

With continuing reference to FIG. 1 and with further reference to FIG. 2, in some embodiments the respiratory marker 40 includes the elongated detectable portion 42, which rests on top of the chest, torso, abdomen, or other portion of the imaging subject 18 so that it falls and rises with the inhalation and exhalation portions of the respiration cycle, respectively. In this embodiment, the operative coupling of the respiratory marker 40 with the imaging subject 18 is achieved by having the elongated detectable portion 42 rest on, and be supported by, the imaging subject 18. Although not shown, the operative coupling may be enhanced by including straps, adhesive, or another connecting mechanism that helps secure the elongated detectable portion 42.

Figure 3:
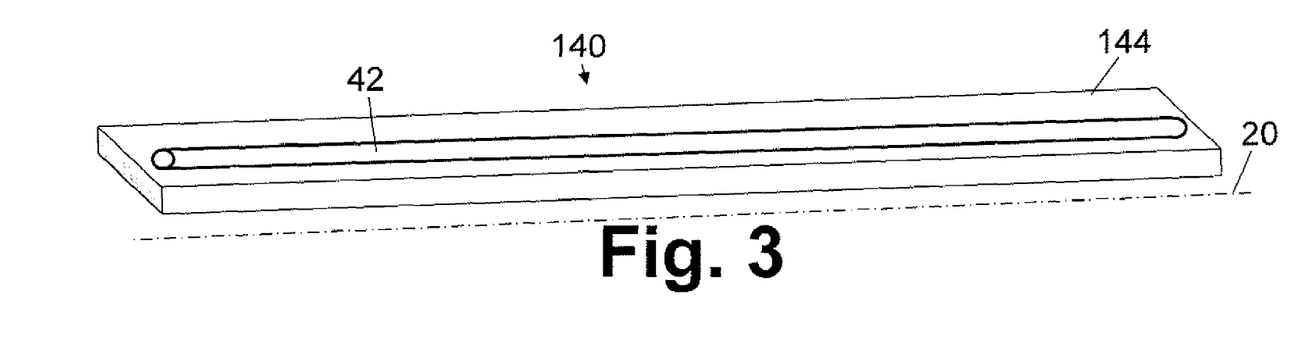
FIG. 3 shows a perspective view of another example respiratory marker.

With reference to FIG. 3, in other embodiments, a respiratory marker 140 resembles the respiratory marker 40, but further includes a spacer portion 144 that is disposed between the elongated detectable portion 40 and the imaging subject 18. The spacer portion 144 in some embodiments has a relatively lower or no visibility in the slice or slab images compared with the elongated detectable portion 40. For example, the spacer portion 144 may be made of a foam material that has relatively low visibility in computed tomography images. A non-magnetic and electrically non-conductive spacer material is suitable for use in a magnetic resonance imaging scanner, as such a material typically has little or no visibility in the acquired magnetic resonance images. The spacer portion 144 provides separation between the elongated detectable portion 40 and the imaging subject 18 that helps in delineating the marker feature corresponding to the elongated detectable portion 40 in the slice or slab images. In this embodiment, the operative coupling of the respiratory marker 140 with the imaging subject 18 is achieved via the spacer portion 144 that operatively couples the elongated detectable portion 42 with the imaging subject 18. Although not shown, the operative coupling may be enhanced by including straps, adhesive, or another connecting mechanism that helps secure the spacer portion 144 to the subject 18. Moreover, the elongated detectable portion 40 may be adhered, bolted, fused to, embedded in, or otherwise fastened to the spacer portion 144. For example, the elongated detectable portion 40 may be embedded within an envelope or jacket of spacer foam.

Figure 4:
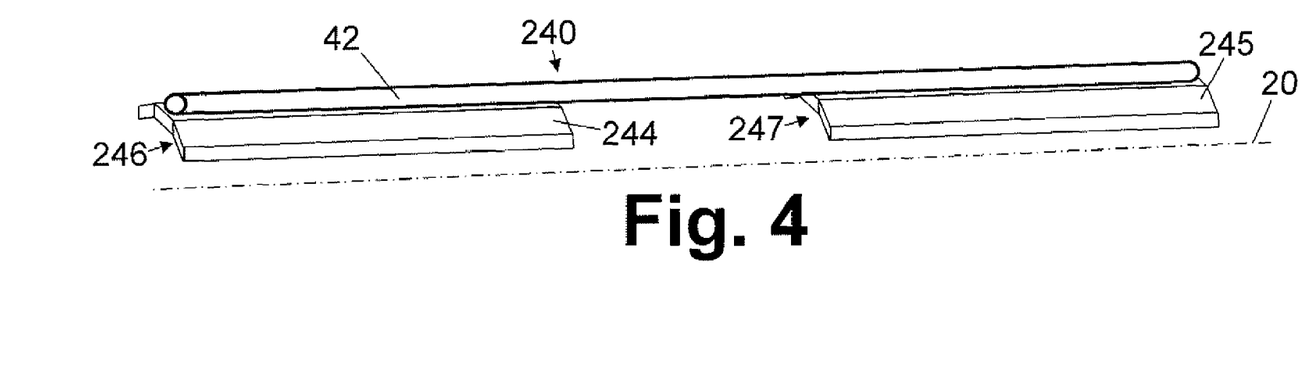
FIG. 4 shows a perspective view of another example respiratory marker.

With reference to FIG. 4, in other embodiments, a respiratory marker 240 resembles the respiratory marker 140, but further includes spacer portions 244, 245 that are spaced apart along the elongated detectable portion 40 and have contours 246, 247 configured to generally conform with the contacted portion of the imaging subject 18. In this embodiment, the operative coupling of the respiratory marker 240 with the imaging subject 18 is achieved via the spacer portions 244, 245 and the contours 246, 247 that operatively couple the elongated detectable portion 42 with the imaging subject 18. Although not shown, the operative coupling may be enhanced by including straps, adhesive, or another connecting mechanism that helps secure the spacer portions 244, 245 to the subject 18. Moreover, the elongated detectable portion 40 may be adhered, bolted, fused to, embedded in, or otherwise fastened to the spacer portions 244, 245. In some contemplated embodiments, the elongated detectable portion 40 is slidably received in one or both of the spacer portions 244, 245.

The respiratory markers 40, 140, 240 include the elongated detectable portion 42, which is typically substantially rigid respective to the forces applied to the marker by the respiring patient, so that at least the elongated detectable portion 42 remains substantially stiff as it moves in correlation with respiration of the patient 18. Some non-rigidity may be acceptable, such as bowing of the elongated detectable portion during certain periods of the respiratory cycle. It is also contemplated to use a non-rigid (i.e., highly flexible) marker such as an elongated cloth of a detectable material that drapes over the patient 18 and moves with the respiration. However, with a highly flexible marker the correlation between movement of the imaged marker feature and the respiratory phase may be more complex, and can be expected to vary with position along the scanner axis 20.

Figure 5:
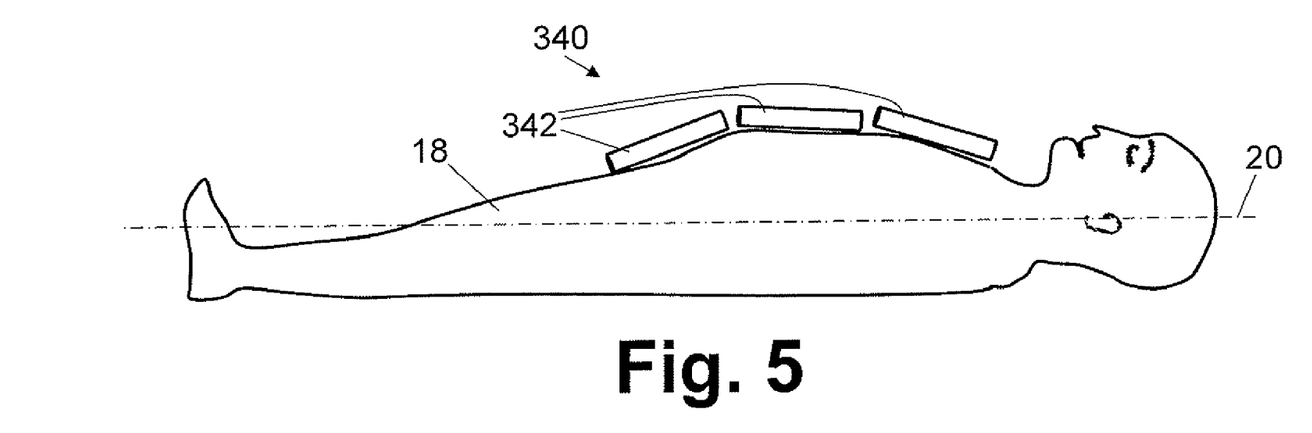
FIG. 5 shows a perspective view of another example respiratory marker disposed with an imaging subject.

With reference to FIG. 5, in some embodiments, a respiratory marker 340 resembles the respiratory marker 40, but has the elongated detectable portion 42 replaced by a plurality of detectable portions 342 that are spaced apart along the scanner axis 20 and move independently responsive to the respiration of the imaging subject 18. The detectable portions 342 may rest directly on the imaging subject 18 as shown in FIG. 5, or may include suitable spacers which may or may not be contoured. The plurality of detectable portions 342 may, for example, include a plurality of elements, pellets, beads, chain elements, a liquid compartments in a contoured tube, or so forth.

Figure 6:
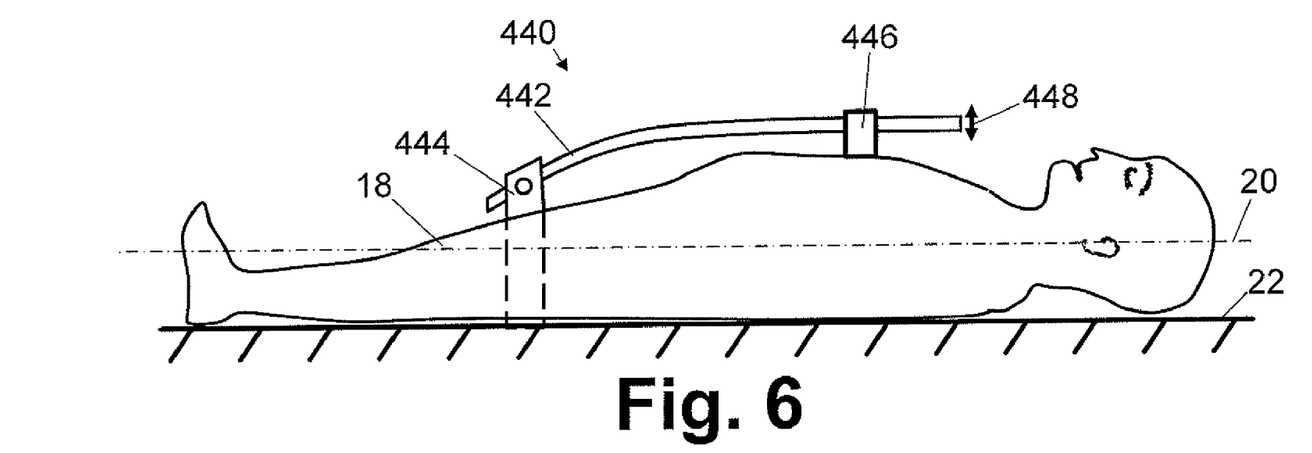
FIG. 6 shows a perspective view of another example respiratory marker disposed with an imaging subject on a subject support.

With reference to FIG. 6, in other embodiments, a respiratory marker 440 has a substantially more complex arrangement. In the example of FIG. 6, a modified elongated detectable portion 442 is not straight, but rather has some curvature that optionally conforms with a curvature of the subject 18. A pivotal connection 444 of an end of the elongated detectable portion 442 is secured to the table 22 of the subject support 16 that supports the imaging subject 18. A subject connection 446 is spaced apart from the pivotal connection 444, and operatively connects the elongated detectable portion 442 with the imaging subject 18 such that the elongated detectable portion 442 pivots (motion indicated by double-headed arrow 448) about the pivotal connection 444 responsive to the respiration of the imaging subject 18. In the example illustrated in FIG. 6, the subject connection 446 is a rest arm or stand that rests on the chest, torso, abdomen, or other portion of the imaging subject 18. Although not shown, the subject connection 446 may be enhanced by including straps, adhesive, or another connecting mechanism that helps secure the subject connection 446 to the subject 18.

With returning reference to FIG. 1, the respiratory marker 40 (or equivalently, one of the example alternative respiratory markers 140, 240, 340, 440) is used to correlate motion or position of the marker 40 with respiratory cycle of the subject 18 to derive the respiration phase or respiratory phase of the subject at the time each image (e.g., each two-dimensional or thin three-dimensional slice image in the case of the illustrated computed tomography scanner 10) was acquired. A marker segmenter 52 processes each image to delineate the marker feature in the image. For example, the segmenter 52 may employ a seeded region-growing algorithm carried out on the images to separate the voxels of the marker feature from voxels imaging the subject 18 or background (e.g., air or other ambient, the table 22, or so forth). The seed is identified in an image manually, for example by pointing and clicking with a mouse in a video display of the image slab or slice shown on the user interface 26, or automatically based for example on expected intensities of voxels of the marker feature. The seeded region-growing algorithm proceeds to aggregate voxels within a selected Hounsfield range within which voxels of the marker feature are expected to lie. The result may be, for example, a binary image in which voxels of the delineated marker feature have value "1" while voxels outside of the segmented marker feature have value "0". It is to be appreciated that, for a two-dimensional slice image or a thin three-dimensional slice image having a small thickness along the direction of the scanner axis, the marker feature is typically a circle, ellipse, or other cross-sectional shape corresponding to the cross-section of the elongated detectable portion 42 of the respiratory marker 40 in the slice image. Having an expected shape and size of the marker feature can expedite the segmentation process and assist in automatically delineating the marker feature.

In embodiments in which a spacer 144, 244, 245 (see FIGS. 3 and 4) is used to space the respiratory marker apart from the patent, this spacing is expected to promote accuracy and speed of the segmentation process. It will be appreciated that these advantages of using the spacer are applicable as well to embodiments in which the detectable portion is not elongated, such as may suitably be the case for use in conjunction with a flat-panel x-ray imager or other imager that does not acquire a plurality of images at different times along an elongated scanning axis. Such embodiments retain the advantage of having the respiratory marker feature integrated with the images (as opposed to having separate image and time indexing datasets), and if the spacer is used, also retain the advantage of having the marker feature spaced apart from the respiring patient in the image so as to facilitate fast and accurate marker feature segmentation.

Once the delineated marker feature is generated by the segmenter 52, a centroid locator 54 locates a centroid of the delineated marker feature. In the case of slice images substantially transversely intersected by an elongated detectable portion having a generally elliptical cross-section, the centroid or other characteristic center point of the delineated marker feature is suitably estimated using an ellipse-fitting algorithm such as that disclosed in Fitzgibbon et al., IEEE Pami 21(5): 476-480 (1999). Other algorithms for finding a centroid or other statistical (e.g., average) position of the delineated marker feature can be used. Algorithms that assume a circular cross-section, rather than an elliptical cross-section, can be used, but will typically be less accurate. If the elongated detectable portion 42 has a non-circular and non-elliptical cross-section, such as a square cross-section, then a suitable centroid-finding algorithm for the particular expected cross-sectional shape can be used. Instead of operating on a binary segmented image, the segmenter 52 can produce a grey scale delineated marker feature representation, and values of the voxels of the delineated marker feature representation can be used as weights for the ellipse-fitting or other centroid-finding algorithm. For example, voxels with a grey scale values relatively closer to the most likely grey scale value may be assigned a higher weight, so as to generally improve the accuracy and robustness of the centroid estimation. The output of the centroid locator 54 for each image is one or more marker feature coordinate values, which are stored in a marker feature coordinates memory 56 along with an index of the image position along the scanner axis 20 and the time (such as an average time) of acquisition of the image. As with the memories 30, 34, the memory 56 can be an electronic, magnetic, optical, or other type of memory.

A retrospective image sorter 60 is configured to sort the slice or slab images by respiratory phase based on the determined marker feature positions stored in the memory 56. Each slice or slab image is annotated with a position along the scanner axis 20, an acquisition time stamp (e.g., an average time of acquisition time stamp), and a centroid position of the marker feature. This information is used to employ a standard retrospective phase- or amplitude-based sorting algorithm, for example as given in Pan et al., MedPhys 31(2):333-340 (2004). The correlation of marker feature position or trajectory in the slice or slab image along at least one dimension with respiratory phase may include adjustment for position along the scanner axis, so as to account for different marker feature trajectories at different points along the scanner axis 20. For example, in the case of the respiratory marker 340 of FIG. 5, the trajectory of marker features associated with each of the independently moving detectable portions 342 is in general different. Similarly, in the case of the respiratory marker 440 of FIG. 6, the trajectories of marker features for slice or slab images located relatively further away from the pivotal connection 444 will generally have larger amplitudes than the trajectories of marker features for slice or slab images located relatively closer to the pivotal connection 444. Once sorted by respiratory phase, slice or slab images having substantially the same assigned respiratory phase are optionally combined to form a volume image representation of said respiratory phase, or spatially coincident slice or slab images having different assigned respiratory phases can be combined to form a temporally varying respiration sequence, or so forth.

Figure 7:
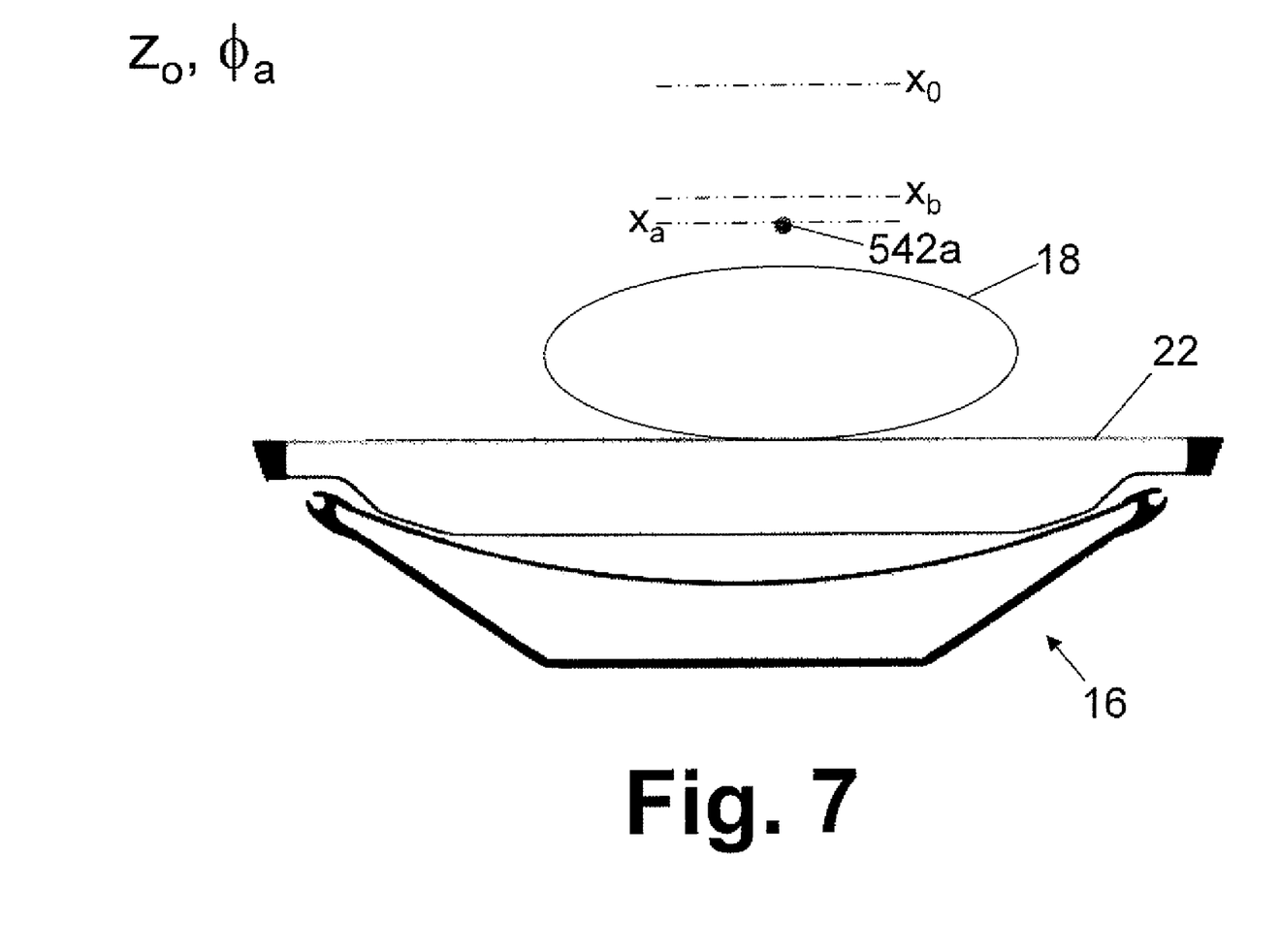
FIG. 7 diagrammatically shows a slice image at a selected position along the scanner axis and at a first respiratory phase close to full exhalation.
Figure 8:
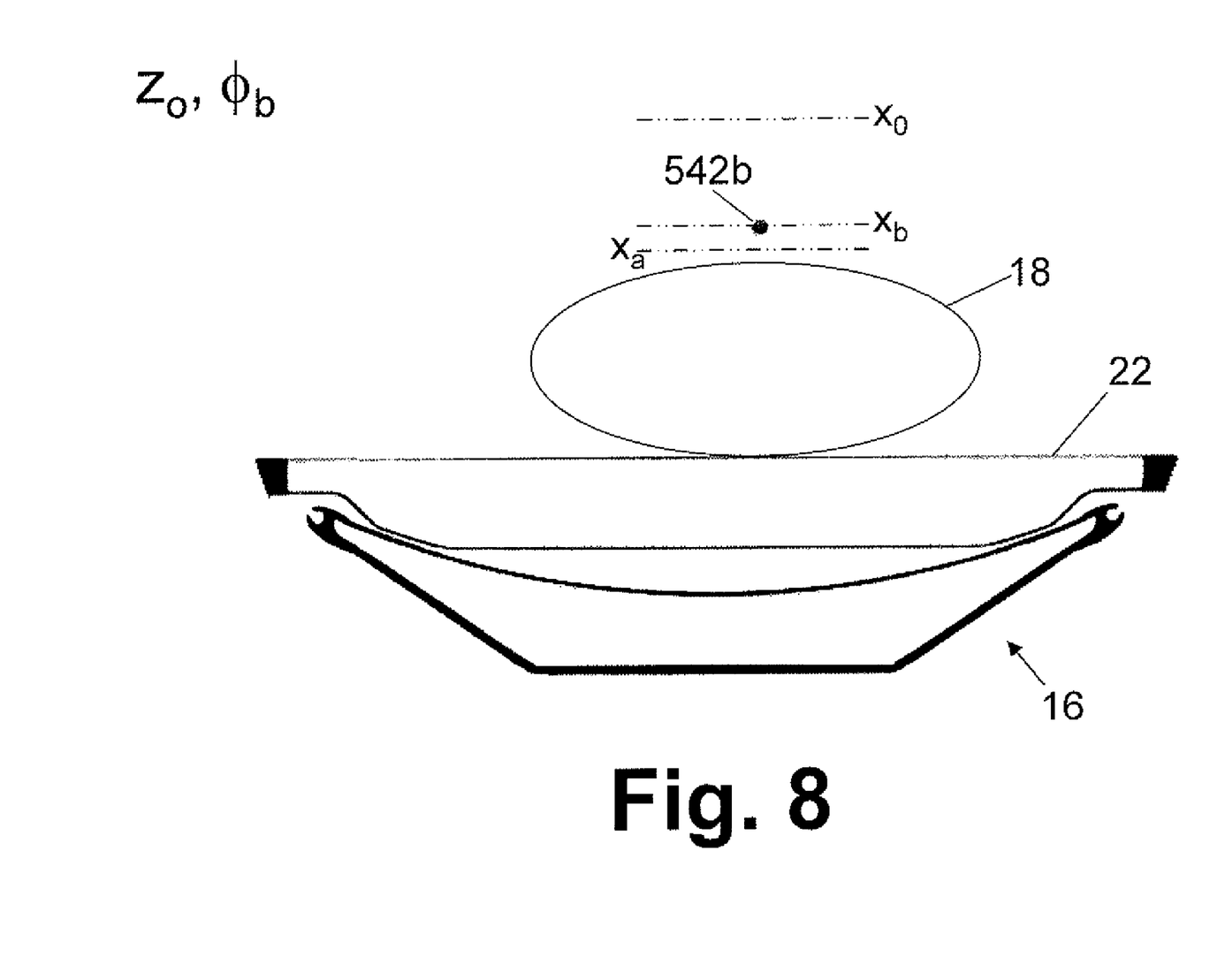
FIG. 8 diagrammatically shows a slice image at the same position along the scanner axis as in FIG. 7, but at a second respiratory phase close to full inhalation.

With reference to FIGS. 7 and 8, example slice images are diagrammatically shown. FIG. 7 diagrammatically shows a slice image acquired at a position denoted $z_o$ along the scanner axis 20 (denoted for this example as the z-axis) and at a respiratory phase denoted $\phi_a$. FIG. 8 diagrammatically shows a slice image acquired at the same position $z_o$ along the scanner axis 20, but at a different respiratory phase denoted $\phi_b$. The slice images have a spatial reference position $x_0$ in the x-direction. For respiratory phase $\phi_a$ (FIG. 7), the marker feature has a centroid 542a at a position $x_a$ respective to the reference position $x_0$. For respiratory phase $\phi_b$ (FIG. 8), the marker feature has a centroid 542b at a position $x_b$ respective to the reference position $x_0$, where $x_b$ is generally different from $x_a$. It will be seen that the position $x_a$ corresponds to the imaging subject 18 having a contracted chest, and corresponds to a point near full exhalation. Similarly, the position $x_b$ corresponds to the imaging subject 18 having an expanded chest, and corresponds to a point near full inhalation. In general, a trajectory of positions between full exhalation ($x_a$) and full inhalation ($x_b$) are expected, and the sorter 60 can assign a respiratory phase to each image based on the position of the centroid relative to its extremes of movement along the x-direction. Although not shown, the trajectory or motion of the centroid may be more complex, for example including motion components in both the x- and y-directions, and such complex trajectories or motions are suitably accounted for in correlating motion with respiratory phase. The reference position $x_0$ may be designated respective to the scanner image coordinates system, or may be designated respective to a fixed-position feature in the image such as the position of the support table 22.

By incorporating the elongated detectable portion 42, 342, 442 into the respiratory marker 40, 140, 240, 340, 440, the respiration is readily tracked as the imaging progresses along the scanner axis 20, since each slice image along the scanner axis 20 will be generally transverse to and intersected by the elongated detectable portion 42, 342, 442. In contrast, a non-elongated marker such as a button or slug marker will be detectable in only one or a few slice images proximate to the button or slug marker. In the arrangement of FIG. 1, the imaging scanner 10 is a computed tomography scanner, and the imaging subject 18 is a human imaging subject arranged such that the slice images are axial slice images. However, the imaging scanner can be a PET, SPECT, or other type of imaging scanner, and the respiring imaging subject can be a human or animal imaging subject. It is to be understood that the slice or slab images are generally transverse to the elongated detectable portion 42, 342, 442, but need not be precisely perpendicular to the elongated detectable portion 42, 342, 442. For example, some imaging scanners can be arranged in a tilted geometry. The Brilliance™ CT scanner, for example, can have the housing 12 (and hence the imaging slices or slabs) tilted respective to the scanner axis 20. Additionally or alternatively, the elongated detectable portion 42, 342, 442 may be tilted or canted respective to the scanner axis 20. For example, the detectable portions 342 of the respiratory marker 340 are not mutually collinear, and the modified elongated detectable portion 442 of the respiratory marker 440 is not straight, but rather has some curvature. Such deviations from a precisely perpendicular arrangement between the slice or slab images and the elongated detectable portion 42, 342, 442 are acceptable as long as the elongated detectable portion 42, 342, 442 is sufficiently transverse to the slice or slab images so that the elongated detectable portion 42, 342, 442 pass through the plurality of slice or slab images so as to provide a marker feature in each slice or slab image.

The components 52, 54, 60 for analyzing the marker features in the images, and for correlating the marker features with respiratory phase, can be physically implemented in various ways. In some embodiments, a storage medium such as a magnetic disk, an optical disk, random access memory (RAM), network server storage, or so forth stores instructions that when executed by a processor implement the components 52, 54, 60 that perform the method for organizing images acquired by the imaging scanner 10 at different times and positions along the scanner axis 20 with the elongated respiratory marker 40, 140, 240, 340, 440 arranged to intersect the images and being detectable as a marker feature in the images. Such a storage medium can be integrated with storage media containing instructions to implement the scanner controller 24, or to implement image display, or so forth, or the same storage medium may store both the respiratory sorting process instructions and instructions to control the scanner, display images, or so forth. In some embodiments, the components 52, 54, 60 for analyzing the marker features in the images are implemented as a stand-alone post-processing system that receives and organizes images previously acquired with the elongated respiratory marker 40, 140, 240, 340, 440 installed. In such a post-processing arrangement, the imaging scanner is modified in that the respiratory marker 40, 140, 240, 340, 440 is installed or loaded with the patient 18, which makes retrofitting existing imaging scanners straightforward. When the analysis components 52, 54, 60 are included in the retrofit, the modification of the existing imaging system is contemplated to additionally include a suitable software upgrade adding the analysis components 52, 54, 60.

In some embodiments, the images in memory 34 are organized as 4D images (for example, with three spatial coordinates such as Cartesian x, y, z coordinates, and a time coordinate t). This provides a full 3D image for each phase and facilitates CINE image displays of individual slices, volumes, surface renderings, and so forth. Corresponding images in different respiratory phases can be subtracted, combined, transformed into a common phase, or so forth.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. An apparatus for organizing two-dimensional or thin three-dimensional axial slice images acquired by a computed tomography scanner at different times and at different positions along a scanner axis, the apparatus comprising:

a respiratory marker including an elongated detectable portion operatively coupled with respiration of a human imaging subject such that the elongated detectable portion moves with the respiration, the elongated detectable portion to intersecting the two-dimensional or thin three-dimensional axial slice images acquired at different times and at different positions along the scanner axis and being detectable as a marker feature in the two-dimensional or thin three-dimensional axial slice images; and a marker position finder configured to determine positions of the marker features in the two-dimensional or thin three-dimensional axial slice images.

2. The apparatus as set forth in claim 1, wherein the marker position finder includes:
   a marker segmenter that segments each acquired image to delineate the marker feature; and
   a centroid locator that locates a centroid of the delineated marker feature.

3. The apparatus as set forth in claim 1, wherein the elongated detectable portion of the respiratory marker extends a full length of an imaged region of the human imaging subject such that a marker feature appears in every two-dimensional or thin three-dimensional axial slice image acquired by the computed tomography scanner at the different times and different positions along the scanner axis.

4. The apparatus as set forth in claim 1, further including:
   a sorter configured to sort the two-dimensional or thin three-dimensional axial slice images by respiratory phase based on the determined marker feature positions.

5. The apparatus as set forth in claim 1, wherein the elongated detectable portion includes an elongated rod.

6. The respiratory marker as set forth in claim 1, wherein the respiratory marker further includes:
   a pivotal connection of an end of the elongated detectable portion to an imaging subject support that supports the human imaging subject; and
   a subject connection spaced apart from the pivotal connection, the subject connection operatively connecting the elongated detectable portion with the human imaging subject such that the elongated detectable portion pivots about the pivotal connection responsive to respiration of the human imaging subject.

7. An apparatus for organizing images acquired by an imaging scanner at different times and at different positions along a scanner axis, the apparatus comprising:
   a respiratory marker including an elongated detectable rod operatively coupled with respiration of an imaging subject such that the elongated detectable rod moves with the respiration, the elongated detectable rod intersecting the images acquired at different times and at different positions along the scanner axis and being detectable as a marker feature in the images;
   a marker position finder configured to determine positions of the marker features in the images; and
   a sorter configured to sort the images by respiratory phase based on the determined marker feature positions.

8. The respiratory marker as net forth in claim 7, wherein the respiratory marker further includes:
   a pivotal connection of an end of the elongated detectable rod to an imaging subject support that supports the imaging subject; and
   a subject connection spaced apart from the pivotal connection, the subject connection operatively connecting the elongated detectable rod with the imaging subject such that the elongated detectable rod pivots about the pivotal connection responsive to respiration of the imaging subject.

9. The apparatus as set forth in claim 7, wherein the elongated detectable rod of the respiratory marker extends a full length of an imaged region of the imaging subject such that a marker feature appears in every image acquired by the imaging scanner at the different times and different positions along the scanner axis.

10. A method for organizing images acquired at different times with a respiratory marker that includes an elongated detectable portion arranged to be detectable as a marker feature in the acquired images, the method comprising:
    arranging the elongated detectable portion generally parallel with a scanning axis such that the elongated detectable portion intersects images acquired at different positions along the scanning axis;
    determining a position of the marker feature in a selected acquired image;
    assigning a respiration phase for the selected acquired image based on the determined position of the marker feature; and
    repeating the determining and assigning operations to assign respiration phases to the images acquired at different times.

11. The method as set forth in claim 10, further including:
    combining images acquired at different times and at different positions along the scanning axis and having substantially the same assigned respiratory phase to form a volume image representation of said respiratory phase.

12. The method as set forth in claim 10, further including:
    combining images acquired at different times and having different assigned respiratory phases to form a temporally varying respiration sequence.

13. The method as set forth in claim 10, wherein the determining includes:
    segmenting the selected image to delineate the marker feature; and
    locating a centroid of the delineated marker feature.

14. A non-transitory digital storage medium storing processor-executable instructions for performing the method as set forth in claim 10.

* * * * *